United States Patent [19]

Murtha

[11] 4,167,456

[45] Sep. 11, 1979

[54] EXTRACTIVE DISTILLATION TO SEPARATE CYCLOHEXYLBENZENE FROM PHENOL-CYCLOHEXANONE MIXTURE CONTAINING THE SAME

[75] Inventor: Timothy P. Murtha, Bartlesville, Okla.

[73] Assignee: Phillips Petroleum Co., Bartlesville, Okla.

[21] Appl. No.: 949,287

[22] Filed: Oct. 6, 1978

[51] Int. Cl.$^2$ .......................... B01D 3/40; C07C 37/38
[52] U.S. Cl. ......................................... 203/63; 568/754
[58] Field of Search ................... 203/50, 56, 63, 38, 203/57; 568/754, 749

[56] References Cited

U.S. PATENT DOCUMENTS

| | | | |
|---|---|---|---|
| 2,575,285 | 11/1951 | Carlson et al. | 203/63 |
| 3,630,855 | 12/1971 | Turbin | 203/63 |
| 4,016,049 | 4/1977 | Fozzard et al. | 203/60 |
| 4,019,965 | 4/1977 | Fozzard | 568/754 |
| 4,021,490 | 5/1977 | Hudson | 568/754 |
| 4,115,204 | 9/1978 | Murtha et al. | 203/60 |
| 4,115,205 | 9/1978 | Murtha | 203/60 |
| 4,115,206 | 9/1978 | Murtha | 203/60 |
| 4,115,207 | 9/1978 | Murtha | 203/60 |

*Primary Examiner*—Wilbur L. Bascomb, Jr.

[57] ABSTRACT

Diaryl ether is used as an extractive distillation solvent to separate mixtures containing cyclohexylbenzene, phenol and cyclohexanone. A mixture of cyclohexylbenzene, cyclohexanone and phenol resulting from the acid catalyzed cleavage of cyclohexylbenzene hydroperoxide is subjected to an extractive distillation with a diaryl ether solvent to obtain removed cyclohexylbenzene as a bottoms fraction.

5 Claims, No Drawings

EXTRACTIVE DISTILLATION TO SEPARATE CYCLOHEXYLBENZENE FROM PHENOL-CYCLOHEXANONE MIXTURE CONTAINING THE SAME

This invention relates to extractive distillation. In one of its aspects the invention relates to the separation of cyclohexylbenzene from a mixture containing it, phenol and cyclohexanone. In another of its aspects the invention relates to the removal of cyclohexylbenzene from the acid catalyzed cleavage of cyclohexylbenzene hydroperoxide.

In one of its concepts the invention provides a method for the extractive distillation-separation of cyclohexylbenzene from a mixture containing it together with phenol and cyclohexanone by subjecting said mixture to extractive distillation conditions employing a diaryl ether solvent. In another of its concepts the invention provides an extractive distillation-separation method for separating cyclohexylbenzene from the acid catalyzed cleavage mass resulting upon such cleavage of cyclohexylbenzene hydroperoxide by subjecting the cleavage mass to extractive distillation conditions in the presence of a diaryl ether solvent.

Cyclohexylbenzene can be converted to phenol and cyclohexanone via cyclohexylbenzene hydroperoxide. The acid catalyzed cleavage of cyclohexylbenzene hydroperoxide in the presence of unoxidized cyclohexylbenzene results in a mixture of cyclohexylbenzene, phenol and cyclohexanone. This mixture is difficult to separate by conventional distillation techniques because phenol and cyclohexanone form an azeotrope (boiling point 185° C. at atmospheric pressure) containing about 72 weight % phenol. In addition, cyclohexylbenzene codistills with this azeotrope.

It is an object of this invention to provide a method for the separation of cyclohexylbenzene from a mixture containing it, cyclohexanone and phenol. It is another object of this invention to provide an extractive distillation-separation method for separating cyclohexylbenzene from a mixture containing it, cyclohexanone and phenol. It is a further object of this invention to provide a method for the extractive distillation-separation of an acid catalyzed cleavage product of cyclohexylbenzene hydroperoxide to remove from said product cyclohexylbenzene and to obtain a purified stream of cyclohexanone and phenol.

Other aspects, concepts and objects of the invention are apparent from a study of this disclosure and the appended claims.

According to the present invention cyclohexylbenzene is separated from cyclohexanone and phenol by subjecting a mixture containing the three components to extractive distillation conditions in the presence of a diaryl ether solvent.

Usually, the solvent is introduced into the top of an extractive distillation tower or unit or an appropriate locus while the mixture to be extractively distilled and separated is introduced at an appropriate locus in a lower portion of the column. The cyclohexylbenzene contained in the diaryl ether solvent is obtained as a bottoms stream.

The diaryl ether can be recovered for recycle from the bottoms stream by fractional distillation.

In the practice of the process of this invention any mixture of phenol, cyclohexanone, and cyclohexylbenzene can be used. It is within the scope of this invention to remove by suitable methods a portion of any of the components from the mixture to be separated before the extractive distillation with the diaryl ethers. For example, any excess of cyclohexanone over the quantity present in the azeotrope can be first distilled from the mixture as essentially pure material. Since cyclohexylbenzene codistills with the phenol/cyclohexanone azeotrope in quantities of about 2 to 10 weight %, any excess of cyclohexylbenzene over that amount can be separated by fractional distillation by taking the phenol-cyclohexanone mixture containing about 2 to 10 weight % cyclohexylbenzene overhead.

Since cyclohexylbenzene and phenol codistill and are difficult to separate, it is also within the scope of this invention to remove essentially all of the cyclohexanone from the mixture by suitable techniques, such as solvent extraction or extractive distillation, before the extractive distillation of this invention.

The diaryl ether solvents to be used in the extractive distillation of this invention will usually contain up to 30 carbon atoms and are represented by the general formula: $R_1$—O—$R_2$ wherein $R_1$ and $R_2$ are each selected from a group consisting of aryl or substituted aryl radicals, with the substituents being one or more of a mixture of alkyl, cycloalkyl, alkoxy, halide, or the like.

Preferably, the boiling point of the solvent will be at least somewhat above the boiling point of cyclohexylbenzene (about 250° C. at atmospheric pressure) to facilitate the separation of the solvent for recycling by fractional distillation. However, low levels of cyclohexylbenzene (up to about 10 weight % cyclohexylbenzene) can be present in the recovered and recycled solvent with no detrimental effect on the extractive distillation. For ease of handling, it is generally preferred that the diaryl ether be a liquid or low melting (below about 80° C.) solid.

Specific examples of diaryl ethers that are suitable for the extractive distillation of this invention include diphenyl ether, di-o-tolyl ether, di-m-tolyl ether, di-p-tolyl ether, 1,4-diphenoxybenzene, bis(4-dodecylphenyl) ether, bis (4-chlorophenyl) ether, phenyl m-tolyl ether, bis(4-methoxyphenyl) ether, bis(4-cyclohexylphenyl) ether, and the like, and mixtures thereof.

The currently preferred solvent for the extractive distillation of this invention is diphenyl ether.

The extractive distillation of this invention can be carried out under a variety of conditions. The volume ratio of diaryl ether to feedstream will be broadly from about 0.01/1 to about 10/1, preferably 0.01/1 to 3.1/1.

To avoid possible thermal decomposition or other reactions during the extractive distillation, head temperatures below about 150° C., preferably below about 110° C., are advantageously used with a reduced pressure sufficient to allow the separation to occur.

In the extractive distillation of this invention, a feed mixture containing phenol, cyclohexylbenzene, and cyclohexanone is fed to a distillation column. As noted, the diaryl ether solvent of this invention is introduced into the extractive distillation column at a point above the point of introduction of the feed mixture. An overhead stream containing phenol and cyclohexanone substantially free of cyclohexylbenzene is withdrawn from the extractive distillation column. The phenol-cyclohexanone overhead stream can be passed to another separation stage to separate this mixture. A bottom stream containing diaryl ether and cyclohexylbenzene is withdrawn from the extractive distillation column and passed to a distillation column.

In the latter distillation column, the cyclohexylbenzene-diaryl ether mixture is separated into an overhead stream containing cyclohexylbenzene and a bottom stream containing diaryl ether. The diaryl ether is recycled to the extractive distillation column and make-up diaryl ether can be added if necessary.

When the mixture to be separated contains phenol and cyclohexylbenzene, e.g., when cyclohexanone has been first removed from a phenol-cyclohexanone-cyclohexylbenzene mixture, the overhead stream from the extractive distillation column will contain phenol substantially free of cyclohexylbenzene.

EXAMPLES

In the following examples, extractive distillations were conducted in an electrically heated 0.75" (19 mm) diameter×36" (914 mm) length column containing 0.25" (6.4 mm) Por-Pak stainless steel perforated screen packing. The solvent was fed through a rotameter and heating section to an introduction port 3" (76 mm) from the top of the column. The mixture to be separated was fed through a rotameter and heating section to an introduction port 18" (457 mm) from the top of the column. The overhead and kettle products were collected and then analyzed by gas-liquid phase chromatography (glpc) on a Hewlett-Packard 5710A chromatograph equipped with a flame ionization detector.

The mixtures to be separated were prepared from commercial, reagent grade phenol and cyclohexanone and cyclohexylbenzene (98% purity) prepared by the reductive alkylation of benzene. The diphenyl ether was a commercially available material.

EXAMPLE I

A run was conducted according to the instant invention utilizing diphenyl ether as the solvent for the extractive distillation of a mixture containing 68 weight % phenol, 27 weight % cyclohexanone, and 5 weight % cyclohexylbenzene. This mixture was fed to the distillation column at a rate of 24 ml/hr. The extractive distillation conditions were 80 mm Hg, 95°-105° C. head temperature, and a 2.8/1 solvent/feed volume ratio. Over a 3.5 hour run time, the overhead fractions contained cyclohexanone and phenol with only about 0.12 weight % cyclohexylbenzene. About 94 weight % of the cyclohexanone and phenol fed to the column during the run was present in the combined overhead fractions. The results of this run demonstrate the removal of cyclohexylbenzene from a mixture of cyclohexylbenzene, phenol, and cyclohexanone by extractive distillation with diphenyl ether.

Example II

Another run was conducted utilizing diphenyl ether as the solvent for the extractive distillation of a mixture containing 68 weight % phenol, 27 weight % cyclohexanone, and 5 weight % cyclohexylbenzene. This run was carried out in a manner similar to the run in Example I except the solvent/feed ratio was increased to demonstrate the effect of a high solvent/feed ratio. The feed mixture was fed to the distillation column at a rate of 28 ml/hr. The extractive distillation conditions were 120 mm Hg, 120°-125° C. head temperature, and a 3.5/1 solvent/feed volume ratio.

Over a 2.2 hour run time, the overhead fractions contained cyclohexanone and phenol with no detectable amounts of cyclohexylbenzene. However, only about 9 weight % of the amount of phenol and cyclohexanone fed to the column during the run was present in the overhead fractions.

The results of this run demonstrate the removal of cyclohexylbenzene from a mixture of cyclohexanone, phenol, and cyclohexylbenzene and show that high solvent/feed volume ratios result in a lower recovery of phenol and cyclohexanone than in Example I.

Reasonable variation and modification are possible within the scope of the foregoing disclosure and the appended claims to the invention the essence of which is that cyclohexylbenzene is separated under conditions of extractive distillation from a mixture containing it, cyclohexanone and phenol employing, as an extractive distillation solvent, a diaryl ether, as described.

I claim:

1. An extractive distillation separation of cyclohexylbenzene from a mixture containing it, cyclohexanone and phenol which comprises subjecting said mixture to extractive distillation conditions employing as a solvent in said distillation a diaryl ether.

2. A method according to claim 1 wherein the diaryl ether solvent can be represented by the formula $$R_1-O-R_2$$

wherein $R_1$ and $R_2$ are selected from the group consisting of aryl and substitute aryl radicals, the substituents being at least one of alkyl, cycloalkyl, alkoxy, and halide.

3. A separation according to claim 1 wherein the boiling point of the diaryl ether solvent is at least somewhat above that of cyclohexylbenzene under the conditions of the operation.

4. A method according to claim 3 wherein the solvent is diphenyl ether.

5. A separation according to claim 1 wherein the mixture separated results from the acid catalyzed cleavage of cyclohexylbenzene hydroperoxide.

* * * * *